United States Patent
Kuras

(10) Patent No.: US 7,857,852 B2
(45) Date of Patent: *Dec. 28, 2010

(54) ARTIFICIAL DISC

(75) Inventor: James Michael Kuras, Macedonia, OH (US)

(73) Assignee: AxioMed Spine Corporation, Willoughby, OH (US)

(*) Notice: Subject to any disclaimer, the term of this patent is extended or adjusted under 35 U.S.C. 154(b) by 1009 days.

This patent is subject to a terminal disclaimer.

(21) Appl. No.: 10/457,589

(22) Filed: Jun. 9, 2003

(65) Prior Publication Data

US 2003/0208271 A1    Nov. 6, 2003

Related U.S. Application Data

(63) Continuation of application No. 09/898,612, filed on Jul. 3, 2001, now Pat. No. 6,607,558.

(51) Int. Cl.
*A61F 2/44* (2006.01)
(52) U.S. Cl. .................................. 623/17.11
(58) Field of Classification Search .......... 623/11.11, 623/16.11, 17.11, 17.12, 17.13, 17.15, 17.16, 623/23.5, 23.53; 606/61
See application file for complete search history.

(56) References Cited

U.S. PATENT DOCUMENTS

| | | | |
|---|---|---|---|
| 4,759,766 A | | 7/1988 | Buettner-Janz et al. |
| 5,002,576 A | * | 3/1991 | Fuhrmann et al. ........ 623/17.15 |
| 5,071,437 A | * | 12/1991 | Steffee .................. 623/17.16 |
| 5,370,697 A | * | 12/1994 | Baumgartner ........... 623/17.15 |
| 5,401,269 A | | 3/1995 | Buttner-Janz et al. |
| 5,458,642 A | | 10/1995 | Beer et al. |
| 5,514,180 A | | 5/1996 | Heggeness et al. |
| 5,534,030 A | | 7/1996 | Navarro et al. |
| 5,645,596 A | | 7/1997 | Kim et al. |
| 5,674,294 A | * | 10/1997 | Bainville et al. ......... 623/17.16 |
| 5,674,296 A | * | 10/1997 | Bryan et al. ............ 623/17.16 |
| 5,702,450 A | * | 12/1997 | Bisserie ................ 623/17.16 |
| 5,755,798 A | | 5/1998 | Papavero et al. |
| 5,824,093 A | * | 10/1998 | Ray et al. ............... 623/17.16 |
| 5,824,094 A | | 10/1998 | Serhan et al. |
| 5,865,846 A | | 2/1999 | Bryan et al. |
| 5,888,226 A | | 3/1999 | Rogozinski |

(Continued)

FOREIGN PATENT DOCUMENTS

EP    1 103 237 A2    5/2001

*Primary Examiner*—Anu Ramana
(74) *Attorney, Agent, or Firm*—Tarolli, Sundheim, Covell & Tummino LLP

(57) ABSTRACT

An artificial disc (10) to replace a damaged spinal disc in a spinal column (16) includes a resilient core (60) having an upper surface (62) and a lower surface (64). An upper retaining member (20) has an outer surface (22) engageable with a first vertebra (12) of the spinal column (16) and an inner surface (24) affixed to the upper surface (62) of the resilient core (60). A lower retaining member (40) has an outer surface (42) engageable with a second vertebra (14) of the spinal column (16) and an inner surface (44) affixed to the lower surface (64) of the resilient core (60). One of the upper and lower retaining members (20, 40) has an opening (30, 50) extending through the outer and inner surfaces into which the resilient core (60) deflects upon relative movement of the upper and lower retaining members (20, 40).

27 Claims, 2 Drawing Sheets

U.S. PATENT DOCUMENTS

| | | | |
|---|---|---|---|
| 5,989,291 A | 11/1999 | Ralph et al. | |
| 6,001,130 A | 12/1999 | Bryan et al. | |
| 6,039,763 A | 3/2000 | Shelokov | |
| 6,113,638 A | 9/2000 | Williams et al. | |
| 6,136,031 A | 10/2000 | Middleton | |
| 6,146,422 A | 11/2000 | Lawson | |
| 6,162,252 A | 12/2000 | Kuras et al. | |
| 6,241,771 B1 | 6/2001 | Gresser et al. | |
| 6,258,126 B1 * | 7/2001 | Colleran | 623/20.29 |
| 6,395,033 B1 | 5/2002 | Pepper | |
| 6,454,806 B1 | 9/2002 | Cohen et al. | |
| 6,468,310 B1 | 10/2002 | Ralph et al. | |
| 6,520,996 B1 * | 2/2003 | Manasas et al. | 623/23.5 |
| 6,582,468 B1 * | 6/2003 | Gauchet | 623/17.16 |
| 6,592,624 B1 * | 7/2003 | Fraser et al. | 623/17.16 |
| 6,602,291 B1 * | 8/2003 | Ray et al. | 623/17.11 |
| 6,645,248 B2 * | 11/2003 | Casutt | 623/17.12 |
| 6,669,732 B2 * | 12/2003 | Serhan et al. | 623/17.16 |
| 7,169,181 B2 * | 1/2007 | Kuras | 623/17.11 |
| 2003/0208270 A9 * | 11/2003 | Michelson | 623/17.11 |

* cited by examiner

ARTIFICIAL DISC

CROSS-REFERENCE TO RELATED APPLICATION

This application is a Continuation of U.S. patent application Ser. No. 09/898,612, filed Jul. 3, 2001 now U.S. Pat. No. 6,607,558.

BACKGROUND OF THE INVENTION

A known artificial disc is disclosed in U.S. Pat. Nos. 6,001,130. U.S. Pat. No. 6,001,130 discloses an artificial disc having a resilient core. Concaval-convex plates at least partly surround the resilient core to retain the core between adjacent vertebral bodies in a spinal column. The concaval-convex plates do not have any openings extending through the plates into which the core deflects.

SUMMARY OF THE INVENTION

An artificial disc to replace a damaged spinal disc in a spinal column includes a resilient core having an upper surface and a lower surface. An upper retaining member has an outer surface engageable with a first vertebra of the spinal column and an inner surface affixed to the upper surface of the resilient core. A lower retaining member has an outer surface engageable with a second vertebra of the spinal column and an inner surface affixed to the lower surface of the resilient core. One of the upper and lower retaining members has an opening extending through the outer and inner surfaces into which the resilient core deflects upon relative movement between the upper and lower retaining members.

BRIEF DESCRIPTION OF THE DRAWINGS

The foregoing and other features of the present invention will become apparent to one skilled in the art to which the present invention relates upon consideration of the following description of the invention with reference to the accompanying drawings, in which.

DESCRIPTION OF THE INVENTION

Figure 1:
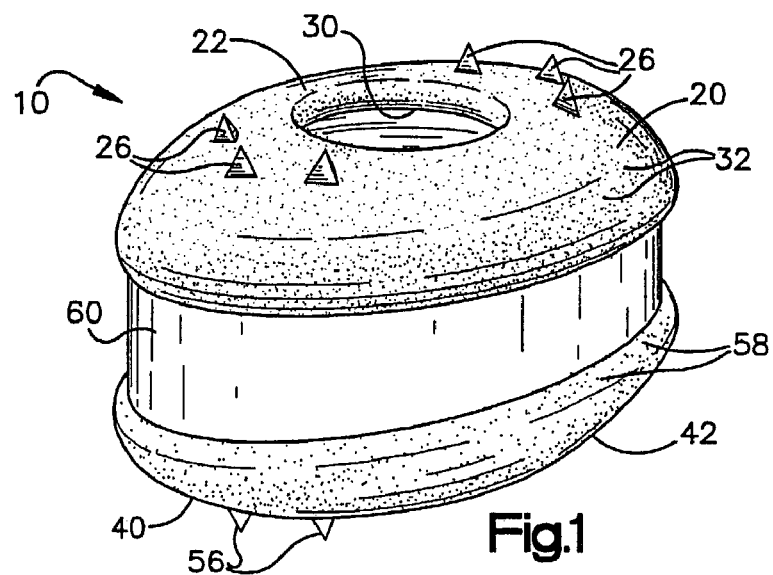
FIG. 1 is a pictorial view of an artificial disc constructed in accordance with the present invention.

The present invention relates to an artificial disc to replace a damaged or degenerated spinal disc in a spinal column of a human. As representative of the present invention, FIG. 1 illustrates an artificial disc 10. The artificial disc 10 (FIG. 4) is used to replace a damaged spinal disc between adjacent upper and lower vertebrae 12 and 14 of a human spinal column 16.

Figure 2:
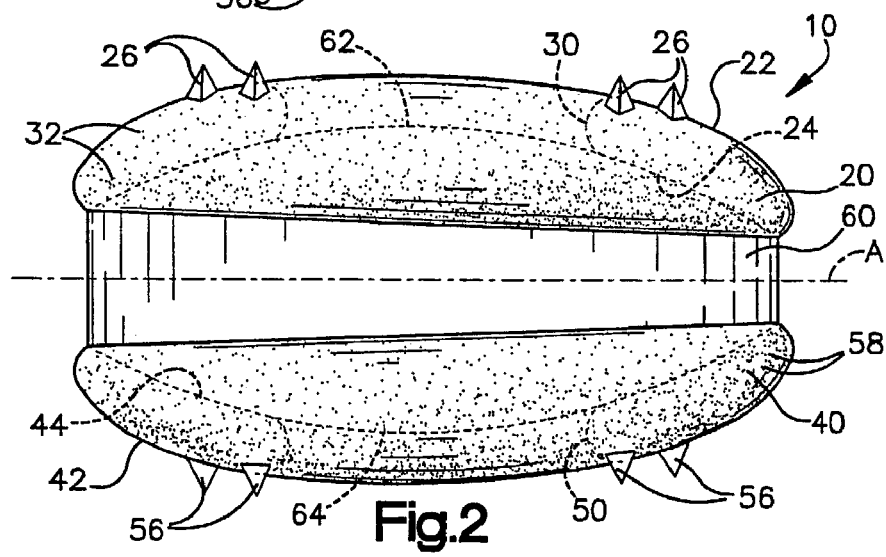
FIG. 2 is a schematic side view of the artificial disc of FIG. 1.
Figure 3:
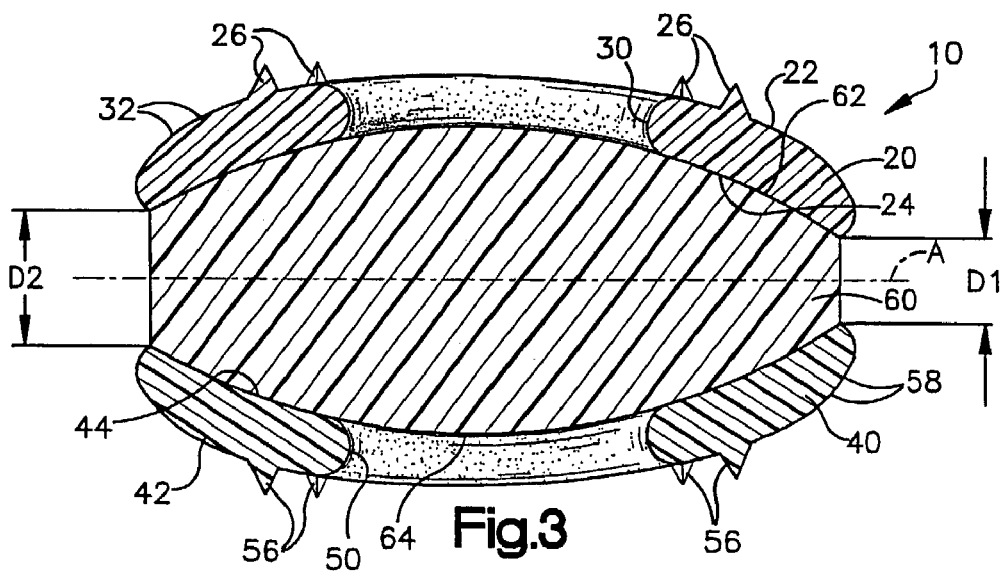
FIG. 3 is a sectional of the artificial disc of FIG. 1.
Figure 4:
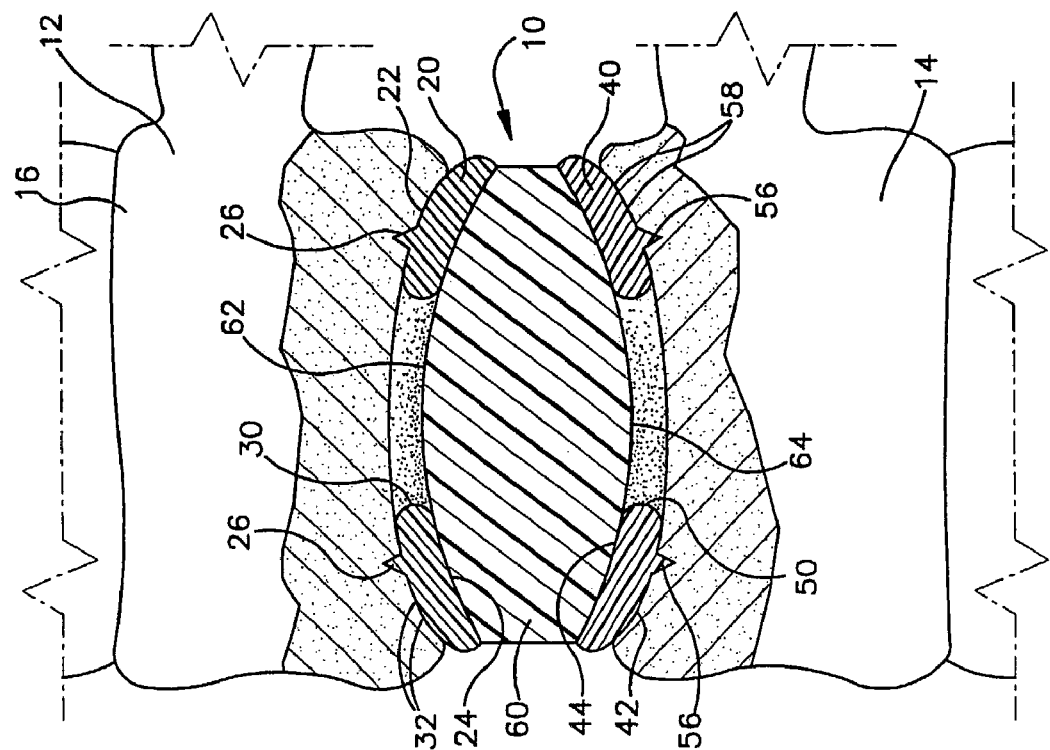
FIG. 4 is a schematic sectional view of the artificial disc of FIG. 1 between adjacent vertebrae of a human spinal column.

The artificial disc 10 (FIGS. 1-3) comprises an upper retaining ring or member 20, a lower retaining ring or member 40 and a resilient core 60 interposed between and adhered or affixed to the two retaining rings. The upper and lower retaining rings 20 and 40 are identical to each other and the disc 10 is symmetrical about a horizontally extending plane A (FIGS. 2 and 3). The terms "upper" and "lower" are used herein with reference to the orientation of the disc 10 when it is implanted in the human body, as illustrated in FIG. 4, to distinguish the two identical retaining rings for reference purposes.

The upper retaining ring 20 is rigid and made of a biocompatible material such as a biocompatible metal or polymer. It is contemplated that the upper retaining ring 20 could be made of titanium. The upper retaining ring 20 (FIGS. 1-4) has an outer convex surface 22 engageable with the vertebra 12. An inner concave surface 24 of the upper retaining ring 20 is affixed to the resilient core 60.

Figure 5:
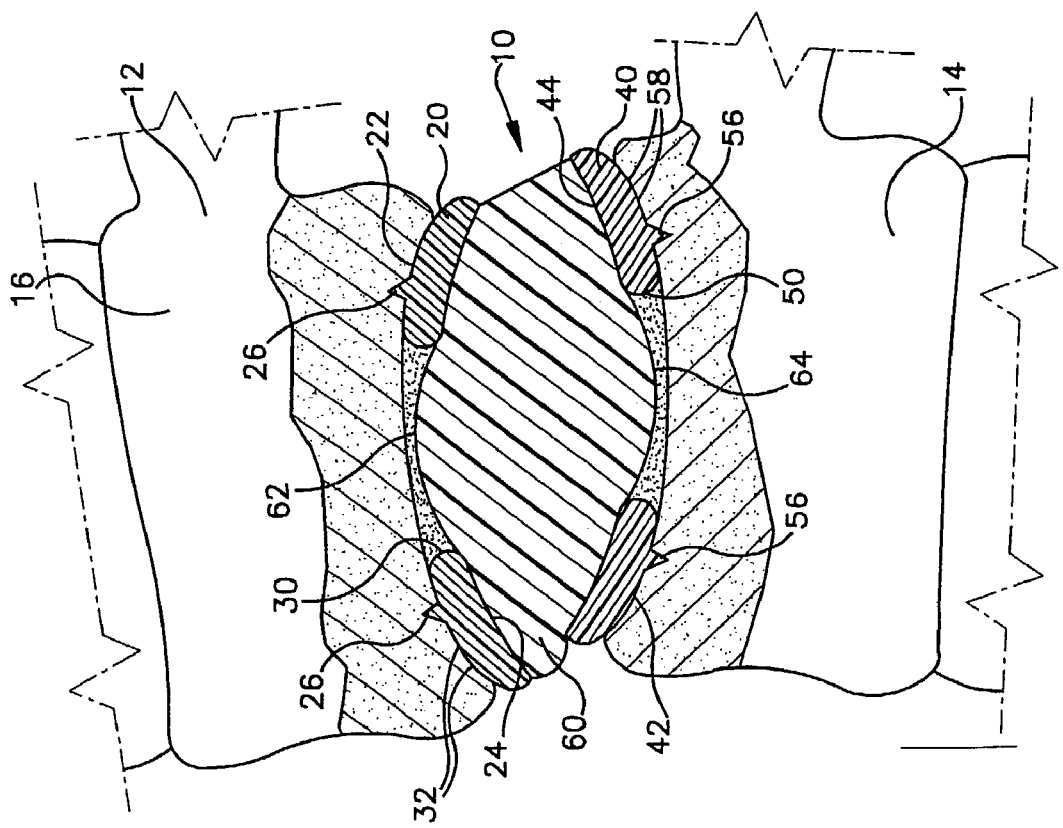
FIG. 5 is a schematic sectional view of the artificial disc between adjacent vertebrae of the spinal column showing the spinal column in flexion.

The upper retaining ring 20 has an axially extending opening 30. The opening 30 extends through the outer surface 22 and the inner surface 24. The resilient core 60 deflects into the opening 30 upon relative movement between the upper and lower retaining rings, such as when the spine 16 is bent in flexion, as shown in FIG. 5. The core 60 expends energy when the core deflects into the opening 30 to limit the amount of stress in the core. Accordingly, the core 60 has a relatively long fatigue life.

Projections 26 extend from the outer surface 22 of the upper retaining ring 20. The projections 26 (FIGS. 4 and 5) engage the vertebra 12 to retain the disc 10 in position between the vertebrae 12 and 14. The outer surface 22 of the upper retaining ring 20 also has beads 32 sintered on the outer surface to further retain the disc 10 between the vertebrae 12 and 14.

The lower retaining ring 40 (FIGS. 2-4) is identical in configuration to the upper retaining ring 20. The lower retaining ring 40 is rigid and made from the same material as the upper retaining ring 20, such as titanium. The lower retaining ring 40 has a convex outer surface 42 engageable with the vertebra 14. An inner concave surface 44 of the lower retaining ring 40 is affixed to the resilient core 60.

The lower retaining ring 40 has an axially extending opening 50. The opening 50 extends through the outer surface 42 and the inner surface 44. The resilient core 60 deflects into the opening 50 upon relative movement between the upper and lower retaining rings 20 and 40, as shown in FIG. 5. The core 60 expends energy when the core deflects into the opening 50 to limit the amount of stress in the core. Accordingly, the core 60 has a relatively long fatigue life.

Projections 56 extend from the outer surface 42 of the lower retaining ring 40. The projections 56 (FIGS. 4 and 5) engage the vertebra 14 to retain the disc 10 in position between the vertebrae 12 and 14. The outer surface 42 also has beads 58 sintered on the outer surface to further retain the disc 10 between the vertebrae 12 and 14.

The resilient core 60 is made of a urethane silicone blend. The resilient core 60 may be adhered or affixed to the upper and lower retaining rings 20 and 40 in any manner known in the art. It is contemplated that the resilient core 60 could be insert molded, transfer molded, or injection molded between the upper and lower retaining rings 20 and 40. The core 60 may be molded between the upper and lower retaining rings 20 and 40 by injecting the material for the core through one of the openings 30 or 50 in the upper and lower retaining rings.

The resilient core 60 is wedge-shaped. The upper retaining ring 20 (FIG. 3) is spaced from the lower retaining ring 40 a first distance D1 adjacent one side of the disc 10. The upper retaining ring 20 is spaced from the lower retaining ring 40 a second distance D2 adjacent another side of the disc 10. The second distance D2 is larger than the first distance D1 so that the resilient core 60 is wedge-shaped.

The core 60 has an upper convex surface 62. The upper convex surface 62 is affixed to the concave inner surface 24 of the upper retaining ring 20. A convex lower surface 64 of the core 60 is affixed to the concave inner surface 44 of the lower retaining ring 40. The concave inner surfaces 24 and 44 limit the amount of stress in the core 60 upon relative movement of the upper and lower retaining rings 20 and 40.

When the disc 10 (FIGS. 4 and 5) is in use in the spinal column 16, the upper retaining ring 20 is affixed to the vertebra 12. The projections 26, the beads 32, and the convex surface 22 resist relative movement between the upper retaining ring 20 and the vertebra 12. The lower retaining ring 40 is affixed to the vertebra 14. The projections 56, the beads 58, and the convex surface 42 resist relative movement between the lower retaining ring 40 and the vertebra 14. When the upper and lower retaining rings 20 and 40 move relative to each other, such as when the spine 16 is bent in flexion, as shown in FIG. 5, the resilient core 60 deflects into the openings 30 and 50 in the retaining rings. Accordingly, the core 60 expends energy to reduce stress in the core upon relative movement of the upper and lower retaining rings 20 and 40 to provide a relatively long fatigue life for the disc 10.

From the above description of the invention, those skilled in the art will perceive improvements, changes and modifications. Such improvements, changes and modifications within the skill of the art are intended to be covered by the appended claims.

Having described the invention, the following is claimed:

1. An artificial disc to replace a damaged spinal disc in a spinal column, said artificial disc comprising:
    a resilient core having an upper surface and a lower surface;
    an upper retaining member having an outer surface engageable with a first vertebra of the spinal column and an inner surface immovably affixed to said upper surface of said resilient core; and
    a lower retaining member having an outer surface engageable with a second vertebra of the spinal column and an inner surface immovably affixed to said lower surface of said resilient core;
    one of said upper and lower retaining members having an opening extending through said outer and inner surfaces of said one of said upper and lower retaining members, said opening being located between the first and second vertebrae when said outer surfaces of said upper and lower retaining members engage the first and second vertebrae, said resilient core deflecting toward said opening extending through said outer and inner surfaces of said one of said upper and lower retaining members upon relative movement between said upper and lower retaining members.

2. An artificial disc as defined in claim 1 wherein said upper retaining member has an opening extending through said inner and outer surfaces of said upper retaining member, said lower retaining member having an opening extending through said inner and outer surfaces of said lower retaining member, said openings extending through said inner and outer surfaces of said upper and lower retaining members being located between the first and second vertebrae when said outer surfaces of said upper and lower retaining members engage the first and second vertebrae.

3. An artificial disc as defined in claim 2 wherein said resilient core deflects toward said opening extending through said outer and inner surfaces of said upper retaining member upon relative movement between said upper and lower retaining members, said resilient core deflecting toward said opening extending through said outer and inner surfaces of said lower retaining member upon relative movement between said upper and lower retaining members.

4. An artificial disc as defined in claim 1 wherein said opening extends axially through said one of said upper and lower retaining members.

5. An artificial disc as defined in claim 1 wherein said upper and lower surfaces of said resilient core are convex and said inner surfaces of said upper and lower retaining members are concave.

6. An artificial disc as defined in claim 1 wherein said outer surfaces of said upper and lower retaining members are convex.

7. An artificial disc as defined in claim 6 wherein said inner surfaces of said upper and lower retaining members are concave, said upper and lower surfaces of said resilient core being convex.

8. An artificial disc as defined in claim 1 further including projections extending from said outer surfaces of said upper and lower retaining members for engaging the first and second vertebrae.

9. An artificial disc as defined in claim 1 wherein said resilient core is wedge-shaped.

10. An artificial disc as defined in claim 1 wherein said resilient core deflects into said opening extending through said outer and inner surfaces of said one of said upper and lower retaining members upon relative movement between said upper and lower retaining members.

11. An artificial disc as defined in claim 1 wherein said resilient core is located adjacent said opening extending through said outer and inner surfaces of said one of said upper and lower retaining members.

12. An artificial disc as defined in claim 1 wherein said upper surface of said resilient core is adhered to said inner surface of said upper retaining member, said lower surface of said resilient core being adhered to said inner surface of said lower retaining member.

13. An artificial disc as defined in claim 1 wherein said core is spaced from said opening when there is no load on said artificial disc.

14. An artificial disc as defined in claim 1 wherein said core is homogeneous.

15. An artificial disc to replace a damaged spinal disc in a spinal column, said artificial disc comprising:
    a resilient core having an upper surface and a lower surface;
    an upper retaining member having an outer surface engageable with a first vertebra of the spinal column and an inner surface immovably affixed to said upper surface of said resilient core; and
    a lower retaining member having an outer surface engageable with a second vertebra of the spinal column and an inner surface immovably affixed to said lower surface of said resilient core;
    an opening extending through the inner surface of one of said upper and lower retaining members, said resilient core deflecting into said opening upon relative movement between said upper and lower retaining members.

16. An artificial disc as defined in claim 15 wherein said upper retaining member has an opening extending through said inner surface of said upper retaining member into which said resilient core deflects upon relative movement between said upper and lower retaining members, said lower retaining member having an opening extending through said inner surface of said lower retaining member into which said resilient core deflects upon relative movement between said upper and lower retaining members.

17. An artificial disc as defined in claim 15 wherein said opening extends axially through said inner surface of said one of said upper and lower retaining members.

18. An artificial disc as defined in claim 15 wherein said upper and lower surfaces of said resilient core are convex and said inner surfaces of said upper and lower retaining members are concave.

19. An artificial disc as defined in claim 15 wherein said outer surfaces of said upper and lower retaining members are convex.

20. An artificial disc as defined in claim 19 wherein said inner surfaces of said upper and lower retaining members are concave, said upper and lower surfaces of said resilient core being convex.

21. An artificial disc as defined in claim 15 further including projections extending from said outer surfaces of said upper and lower retaining members for engaging the first and second vertebrae.

22. An artificial disc as defined in claim 15 wherein said resilient core is wedge-shaped.

23. An artificial disc as defined in claim 15 wherein said resilient core is located adjacent said opening extending through said inner surface of said one of said upper and lower retaining members.

24. An artificial disc as defined in claim 15 wherein said opening extends through the inner surface and the outer surface of said one of said upper and lower retaining members.

25. An artificial disc as defined in claim 15 wherein said core is spaced from said opening when there is no load on said artificial disc.

26. An artificial disc as defined in claim 15 wherein said core is homogeneous.

27. An artificial disc to replace a damaged spinal disc in a spinal column, said artificial disc comprising:

- a resilient core having an upper surface and a lower surface;
- an upper retaining member having an outer surface engageable with a first vertebra of the spinal column and an inner surface immovably affixed to said upper surface of said resilient core; and
- a lower retaining member having an outer surface engageable with a second vertebra of the spinal column and an inner surface immovably affixed to said lower surface of said resilient core;
- said upper retaining member having a first opening extending through said inner and outer surfaces of said upper retaining member, said lower retaining member having a second opening extending through said inner and outer surfaces of said lower retaining member, said first and second openings being located between the first and second vertebrae when said outer surfaces of said upper and lower retaining members engage the first and second vertebrae, said resilient core deflecting toward said first and second openings upon relative movement between said upper and lower retaining members.

* * * * *